United States Patent [19]

Aziz et al.

[11] Patent Number: 4,909,803
[45] Date of Patent: Mar. 20, 1990

[54] DISPOSABLE ABSORBENT ARTICLE HAVING ELASTICIZED FLAPS PROVIDED WITH LEAKAGE RESISTANT PORTIONS

[75] Inventors: Mohammed I. Aziz, Cincinnati; Ted L. Blaney, West Chester, both of Ohio

[73] Assignee: The Procter and Gamble Company, Cincinnati, Ohio

[21] Appl. No.: 316,123

[22] Filed: Feb. 24, 1989

Related U.S. Application Data

[63] Continuation of Ser. No. 690,298, Jan. 10, 1985, Pat. No. 4,808,178, which is a continuation of Ser. No. 510,467, Jun. 30, 1983, abandoned, which is a continuation of Ser. No. 308,017, Oct. 5, 1981, abandoned.

[51] Int. Cl.$^4$ .............................................. A61F 13/16
[52] U.S. Cl. .................................................. 604/385.2
[58] Field of Search ................... 604/385.2, 385.1, 372, 604/373, 378, 389, 390

[56] References Cited

U.S. PATENT DOCUMENTS

| Re. 26,151 | 1/1967 | Duncan et al. . | |
|---|---|---|---|
| 2,545,674 | 3/1951 | Ralph . | |
| 3,452,753 | 7/1969 | Sanford | 604/385 |
| 3,572,342 | 3/1971 | Lindquist et al. . | |
| 3,658,064 | 4/1972 | Pociluyko . | |
| 3,779,167 | 3/1974 | Miller et al. | 604/385 X |
| 3,807,402 | 4/1974 | Miller et al. | 604/385 X |
| 3,860,003 | 1/1975 | Buell | 604/385.1 |
| 3,952,745 | 4/1976 | Duncan . | |
| 3,967,623 | 7/1976 | Butterworth et al. . | |
| 3,999,548 | 12/1976 | Hernandez . | |
| 4,050,462 | 9/1977 | Woon et al. . | |
| 4,210,143 | 7/1980 | DeJonckheere | 604/370 |
| 4,246,900 | 1/1981 | Schroder . | |
| 4,282,874 | 8/1981 | Mesek . | |
| 4,300,562 | 11/1981 | Pienak | 604/373 |
| 4,337,771 | 7/1982 | Pieniak et al. . | |
| 4,352,355 | 10/1982 | Mesek et al. . | |
| 4,397,645 | 8/1983 | Buell | 604/385.1 |
| 4,427,408 | 1/1984 | Karami et al. | 604/385 |
| 4,490,148 | 12/1984 | Beckestrom | 604/385.1 |
| 4,695,278 | 9/1987 | Lawson | 604/385 X |
| 4,808,178 | 2/1989 | Aziz et al. . | |

FOREIGN PATENT DOCUMENTS

| 866527 | 10/1978 | Belgium . |
| 0091412 | 10/1988 | European Pat. Off. . |
| 41-18031 | 8/1966 | Japan . |
| 2016262 | 9/1979 | United Kingdom . |
| 2023431 | 1/1980 | United Kingdom . |

*Primary Examiner*—John D. Yasko
*Attorney, Agent, or Firm*—Steven W. Miller; John M. Pollaro; Fredrick H. Braun

[57] ABSTRACT

A disposable absorbent article for absorbing liquids, particularly body fluids such as urine. An absorbent core is encased in an outer covering layer to which flaps are connected along the longitudinal sides at a proximal edge. The flaps also have a distal edge which is displaced from the absorbent core means. The flaps are elasticized to render the distal edge elastically contractible so that the flap is gathered.

28 Claims, 3 Drawing Sheets

DISPOSABLE ABSORBENT ARTICLE HAVING ELASTICIZED FLAPS PROVIDED WITH LEAKAGE RESISTANT PORTIONS

This is a continuation of application Ser. No. 690,298, filed on January 10, 1985 now U.S. Pat. No. 4,808,178; which is a continuation of application Ser. No. 510,467, filed on June 30, 1983 now abandoned; which is a continuation of application Ser. No. 308,017, filed on October 5, 1981 now abandoned.

BACKGROUND OF THE INVENTION

This invention relates to disposable absorbent articles in general and more particularly relates to disposable diapers and the like. Still more particularly, this invention relates to disposable diapers having a multiplicity of flaps along the longitudinal sides of the absorbent core in which the flaps have an elastically contractible distal edge, a fixed edge and a non-wicking, non-absorbent, liquid impermeable leakage resistant member interposed between the distal and fixed edges on the liquid contacting surface.

Disposable absorbent articles are well known and have many uses. For example, disposable diapers are intended to absorb and contain urine; bandages are intended to absorb and contain blood and other body exudates; while catamenial pads are intended to absorb and retain menstrual fluids. In each instance, the disposable absorbent article absorbs and retains a liquid, thereby preventing that liquid from soiling wetting, or otherwise contaminating the vicinity surrounding the point of liquid discharge. For example, U.S. Pat. No. Re. 26,151 which is issued on January 31, 1967 to R. C. Duncan et al. entitled "Disposable Diaper" teaches a disposable diaper intended to absorb urine and prevent the wetting of the wearer's clothing.

Disposable absorbent articles should perform without leaking and several concepts have been proposed to improve the liquid containment characteristics of disposable absorbent articles such as disposable diapers. U.S. Pat. No. 3,999,548 entitled "Disposable Diaper Having Fluid Trap" which issued to J. Hernandez on December 28, 1976 teaches that the liquid containment characteristics of a diaper can be improved by securing sealing strips of waterproof material to the face sheet of the diaper. Alternatively, U.S. Pat. No. 3,860,003 entitled "Contractible Side Portions For A Disposable Diaper" which issued to K. B. Buell on January 14, 1975 and U.S. Pat. No. 4,050,462 entitled "Disposable Diaper With Elastically Constricted Crotch Section" which issued to L. S. Woon et al. on September 7, 1977 both teach a concept for reducing liquid leakage which involves providing an elastic member in a disposable diaper. The elastic member is positioned so that when the diaper is worn, the diaper is drawn snugly about the legs of the wearer. The elastic causes the diaper to form a seal about the leg of the wearer thereby preventing liquid from leaking out of the diaper.

The disposable absorbent articles of the prior art lack the aspects of the present invention whereby an improvement in the liquid containment characteristics is obtained by providing elastically contractible flaps along the longitudinal sides of the article which flaps have a leakage resistant portion which is non-wicking, non-absorbent, and liquid impermeable.

It is therefore an object of the present invention to provide a disposable absorbent article having improved liquid containment characteristics.

A further object of the present invention is to provide a disposable absorbent article having elastically contractible flaps provided with a leakage resistant portion which is non-wicking, non-absorbent, and liquid impermeable.

These and other objects of the invention will be more readily apparent when considered in reference to the following description and when taken in connection with the accompanying drawings.

SUMMARY OF THE INVENTION

According to the present invention, a disposable absorbent article such as a diaper is manufactured such that a liquid absorbent core is encased in an outer covering layer having a liquid permeable topsheet portion and a liquid impermeable backsheet portion. The disposable absorbent article is provided with a multiplicity of flaps which fit about the legs of the wearer when the diaper is worn. The flaps have a fixed edge connected to the outer covering layer, an elasticized distal edge spaced from the fixed edge, and a liquid contacting surface across which liquid must flow to move from the fixed edge to the distal edge.

A leakage resistant portion which is non-wicking, non-absorbent and liquid impermeable is interposed on the liquid contacting surface of the flaps, between the fixed and distal edges. Thus, in order for liquid to flow or wick from the point of discharge to the distal edge where liquid leakage about the legs can occur it is necessary for the liquid to move across the leakage resistant portion. The leakage resistant portion is non-wicking and non-absorbent which characteristics prevent liquid from reaching the distal edge of the flap from which leakage from the diaper can occur.

DESCRIPTION OF A PREFERRED EMBODIMENT

Referring now to the figures, there is shown a preferred embodiment of the present invention as it would be used in a disposable absorbent article and, in particular, as it would be used in a disposable diaper. As used herein, the term disposable absorbent article refers to articles which absorb and contain liquid, and more specifically refers to articles which are placed against or in proximity to the human body to absorb and contain the various liquids discharged therefrom (e.g., blood, menses, urine, etc.), and further which articles are intended to be discarded after a single use (i.e., they are not intended to be laundered or otherwise restored and reused). A "diaper" is a garment generally worn by infants or incontinent persons, which is drawn up between the legs and fastened about the waist of the user. It should be understood, however, that the present invention is also applicable for use in other disposable absorbent articles such as bandages, catamenial pads, and the like.

Figure 1:
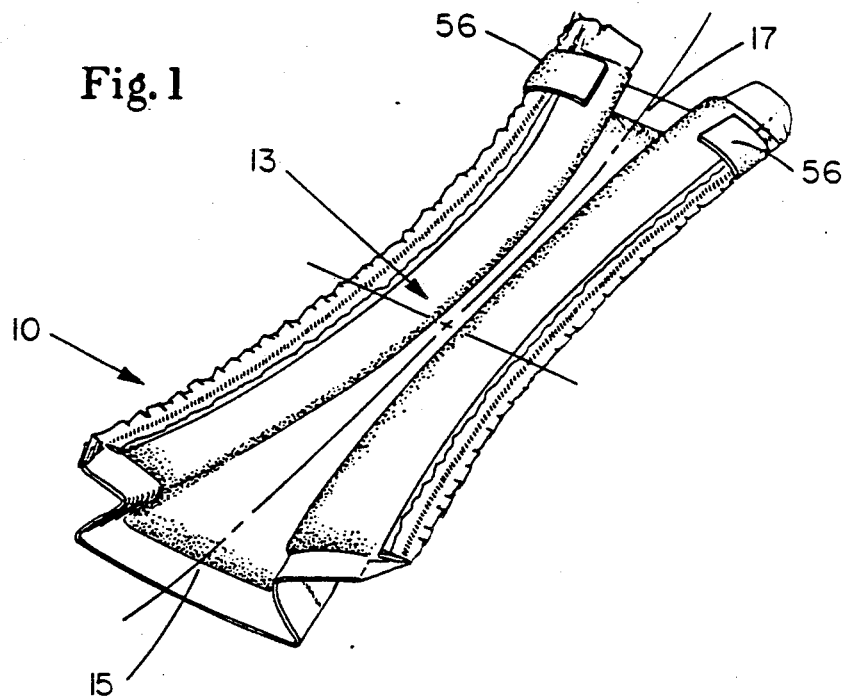
FIG. 1 is a perspective view of a disposable diaper which incorporates the present invention and which is Z-folded and ready to be placed on an infant.

FIG. 1 is a perspective view of a diaper 10 having a Z-folded side configuration and incorporating the features of the present invention. As shown in FIG. 1 the diaper 10 is in condition for placement on a wearer. In general, the crotch portion 13 of the diaper 10 is placed between the wearer's legs and the front and back waist portions 15 and 17 respectively, are joined together by adhesive tapes 56 so as to encircle the wearer's waist and to hold the diaper 10 in place. While the present invention will be described with reference to a diaper having a Z-folded side configuration, it should be understood that diaper configurations and constructions other than those specifically described, such as C-folded and unfolded side configurations, may also incorporate the features of the present invention.

Figure 2:
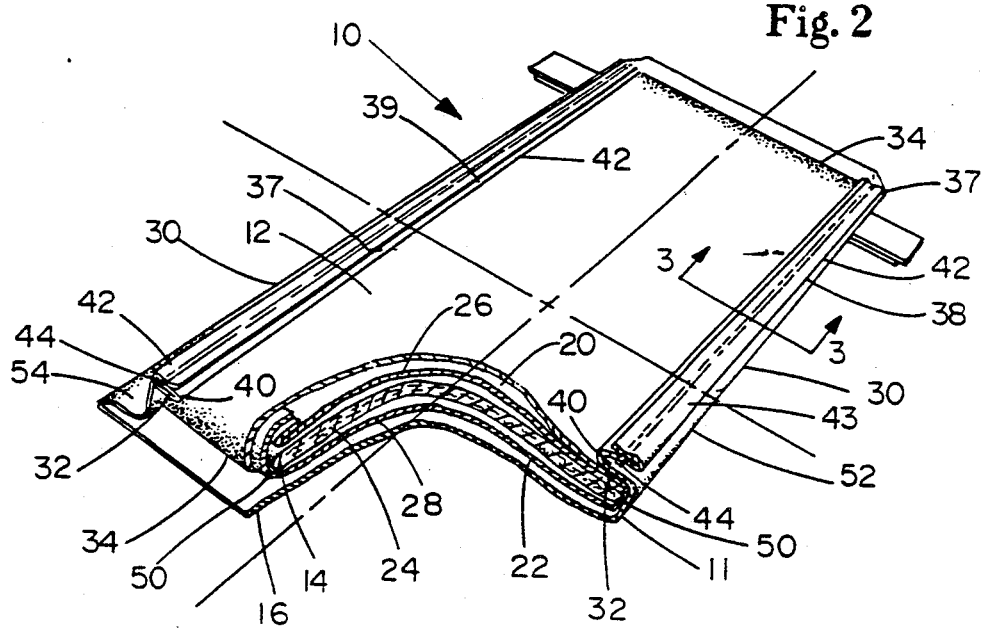
FIG. 2 is a partially cut away perspective view of the disposable diaper of FIG. 1 prior to being Z-folded and contracted.

To simplify the description of the present invention the diaper 10 of FIG. 1 is shown in FIG. 2 in a partially cut-away perspective view prior to its being Z-folded, contracted, and placed on the diaper wearer. As seen in FIG. 2, a preferred disposable diaper 10 basically comprises an outer covering layer 11 and an absorbent core 14. While the outer covering layer 11 and the absorbent core 14 may be assembled in a variety of well known configurations, such as are described generally in U.S. Patent No. Re. 26,151 entitled "Diaper" which issued to R. C. Duncan et al. on January 31, 1967, and in U.S. Pat. No. 3,860,003 entitled "Contractible Side Portions For Disposable Diaper" which issued to K. B. Buell on January 14, 1975, which patents are incorporated herein by reference, a preferred construction of the diaper 10 will now be described.

Figure 3:
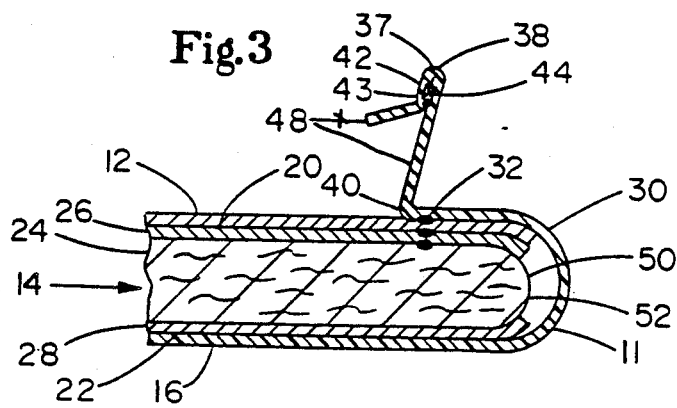
FIG. 3 is a cross-sectional view of the diaper of FIG. 2 taken along line 3—3.

As can be seen in FIGS. 2 and 3, a preferred outer covering layer 11 encases and contains the absorbent core 14 and preferably has a topsheet portion 12 and a backsheet portion 16 which are joined together in any suitable matter. As used herein, the term "joined" encompasses configurations whereby the topsheet portion 12 is directly joined to the backsheet portion 16 by affixing the topsheet portion 12 directly to the backsheet portion 16 and configurations whereby the topsheet portion 12 is indirectly joined to the backsheet portion 16 by affixing the topsheet portion 12 to intermediate members which in turn is affixed to the backsheet portion 16. In the preferred embodiment of FIGS. 2 and 3, the topsheet portion 12 and the backsheet portion 16 are joined directly to each other.

The absorbent core 14 may be any means which is generally compressible, conformable, non-irritating to the wearer's skin, and which is capable of absorbing and retaining liquids. A preferred absorbent core 14 has first and second opposed faces 20 and 22 respectively, and comprises an absorbent layer 24 and first and second tissue layers 26 and 28 respectively. The first and second tissue layers 26 and 28 overlay the major surfaces of the absorbent layer 24 to form first and second opposed faces 20 and 22. The outer periphery of the absorbent core 14 forms a peripheral edge 50 having first and second longitudinal side edges 52 and 54 respectively.

The absorbent layer 24 may be manufactured in a wide variety of sizes and shapes (e.g., rectangular, hourglass, etc.) and from a wide variety of liquid absorbent materials commonly used in disposable absorbent articles, such as comminuted wood pulp which is generally referred to as absorbent fluff. Other liquid absorbing materials can also be used for the absorbent layer 24, such as a multiplicity of plies of crepe, cellulose wadding, absorbent foams or sponges, or any equivalent material. Further, the size and absorbent capacity of the absorbent layer 24 may be varied to accommodate wearer's ranging from infants to adults. The preferred embodiment illustrated in FIGS. 2 and 3 has a rectangular absorbent layer 24 and is intended for infants of from about 12 pounds to about 23 pounds (about 5 kilograms to about 10 kilograms). The absorbent layer 24 is, therefore, absorbent fluff approximately 12 inches (31.8 centimeters) wide by 16 inches (40.6 centimeters) long having an absorbent capacity of from 8 to 16 grams of water per gram of absorbent. Accordingly, the absorbent fluff used in the preferred embodiment shown in FIGS. 2 and 3 weighs approximately from 30 to 56 grams. It should be understood, however, that the size, shape, and total absorbent capacity of the absorbent core 14 may be varied to accommodate wearers ranging from infants to adults. Therefore, other dimensions and even other shapes (e.g., hourglass) may also be used for the absorbent core 14.

The tissue layers 26 and 28 improve the tensile strength of the absorbent core 14 and reduce the tendency of the absorbent layer 24 to split, lump or ball when wetted. The tissue layers 26 and 28 also help to improve lateral wicking of absorbed liquids, thereby providing a more even distribution of liquids throughout the absorbent core 14. While a number of materials and manufacturing techniques may be used to manufacture the tissue layers 26 and 28, satisfactory results have been obtained with sheets of tissue paper having a basis weight of from about 10 pounds per 3,000 square feet (16 grams per square meter) and having an air permeability of about 100 cubic feet per minute per square foot (30.5 cubic meters per minute per square meter) over a ½ inch (12.8 millimeter) water pressure drop. While the tissue layers 26 and 28 are preferably coterminous with the absorbent layer 24, they may have different dimensions, a different configuration, or they may be omitted entirely.

The second tissue layer 28 is superimposed on the backsheet portion 16 and is preferably attached thereto by attachment means (not shown) such as those well known in the art. For example, the absorbent core 14 can be secured to the backsheet portion 16 by a uniform continuous layer of adhesive, a patterned layer of adhesive, or an array of separate lines or spots of adhesive. An adhesive which has been found to be satisfactory is manufactured by Eastman Chemical Products Company of Kingsport, Tennessee and marketed under the tradename Eastobond A-3.

The backsheet portion 16 is impervious to liquids and is preferably manufactured from a thin plastic film, although other flexible liquid impervious materials may also be used. The backsheet portion 16 prevents the liquids contained in the absorbent core 14 from wetting articles which contact the diaper, such as bedsheets and undergarments. Polyethylene films having a thickness of from about 0.0005 to about 0.002 inches (0.0012 to 0.0051 centimeters) have been used for the backsheet portion 16 in a preferred embodiment with satisfactory results. As used herein, the term "flexible" refers to materials which are compliant and which will readily conform to the general shape and contours of the human body. A suitable polyethylene film is manufactured by Monsanto Chemical Company and marketed in the trade as film No. 8020.

The topsheet portion 12 is compliant, soft feeling, and non-irritating to the wearer's skin. Further, the topsheet portion 12 is liquid permeable, permitting liquids to readily penetrate through its thickness. A suitable topsheet 12 may be manufactured from a wide range of materials such as porous foams, apertured plastic films, natural fibers (e.g., wood or cotton fibers), synthetic fibers (e.g., polyester or polypropylene fibers) or from a combination of natural and synthetic fibers and prevents the wearer of the diaper 10 from contacting the absorbent core 14.

A particularly preferred topsheet portion 12 comprises by weight about 65 percent staple length polyester fibers having a denier of about 1.5, such as Kodel-type 411 polyester fibers marketed by Tennessee Eastman Corporation of Kingsport, Tennessee; about 15 percent staple length crimped rayon fibers having a denier of about 1.5; and about 20 percent acrylic copolymer binder such as Celanese CPE 8335 marketed by Celanese Corporation of Charlotte, North Carolina. As used herein, the term "staple length fibers" refers to those fibers having a length of at least ⅝ inches (15.9 millimeters).

Clearly, there are a number of manufacturing techniques which may be utilized to manufacture the topsheet portion 12. For example, the topsheet portion 12 may be woven, non-woven, spun-bonded, carded or the like. A perferred topsheet portion 12 is carded, saturated with a binder solution, dried and cured by means well known to those skilled in the art. Preferably, the topsheet portion 12 has a basis weight range of from about 18 to about 22 grams per square yard. A preferred topsheet portion 12 is further characterized by a minimum wet tensile strength of at least about 400 grams per centimeter in a machine direction and at least about 55 grams per centimeter in a cross machine direction.

The backsheet portion 16 is superimposed on the second opposed face 22 of the absorbent core 14 and has dimensions generally larger than those of the absorbent core 14. The topsheet portion 12 is superimposed on first opposed face 20 of the absorbent core 14 and is coterminous with the first and second longitudinal side edges 52 and 54, respectively, but is longer than the absorbent core 14. The longitudinal margins 30 of the backsheet portion 16 are folded onto and affixed to the topsheet portion 12 along the longitudinal seams 32 in any suitable manner such as by the use of adhesives. A suitable adhesive is manufactured by National Starch Corporation of Bridgewater, New Jersey and marketed under the tradename Instant Lock 34-2933, although other adhesive as are well known may also be used. As best seen in FIG. 2, transverse edges 34 of the topsheet portion 12 are folded onto the second opposed face 22 of the absorbent core 14 and affixed to the backsheet portion 16 along transverse seams (not shown). The absorbent core 14 is, therefore, encased within the outer covering layer 11 which comprises the backsheet portion 16 and the topsheet portion 12, the backsheet portion 16, and the absorbent core 14 may be assembled into a disposable diaper is given in the hereinbefore referenced U.S. Pat. No. Re. 26,151 entitled "Disposable Diaper" which issued to R. C. Duncan et al. on January 31, 1967.

Liquid discharged onto the diaper 10 while it is being worn will tend to be distributed throughout the diaper 10. As a result of the liquid distribution some of the liquid will move toward segments of the diaper 10 from which leakage can occur. The location of these segments and the specific means by which leakage occurs will depend on the particular construction used for the diaper 10. In general, however, liquid leakage frequently occurs at those segments of the diaper 10 which are fitted about the legs of the diaper wearer.

The figures illustrate a preferred embodiment and alternatively preferred embodiments of the present invention in which liquid leakage around the legs of the diaper wearer is to be reduced. Accordingly, the diaper 10 illustrated in FIGS. 2 and 3 is provided with a multiplicity of flaps 37 positioned so as to encircle the legs of the wearer when the diaper is worn. While it is not essential that the legs be completely encircled, the preferred embodiment shown in FIG. 2 has flaps 37 traversing the entire length of the diaper 10.

The flaps 37 are thin, flexible bands having a fixed edge 40, a distal edge 42, and a liquid contacting surface 43. The fixed edge 40 and the distal edge 42 are in spaced relation to each other and define the width of the flaps 37. The fixed and distal edges 40 and 42 may be parallel, non-parallel, rectilinear or curvilinear. Preferably, however, the distal and fixed edges 42 and 40 are parallel and rectilinear thereby imparting a uniform width to the flaps 37. The liquid contacting surface 43 is the major surface the longitudinal sides of which are bounded by the fixed and distal edges 40 and 42 by the fixed and distal edges 40 and 42 and across which surface urine (as hereinafter defined) must flow to move from the fixed edge 40 to the distal edge 42.

The preferred diaper 10 illustrated in FIG. 2 is provided with a first flap 38 and with a second flap 39 each having a fixed edge 40 connected to the outer covering layer 11 at the first longitudinal side edge 52 and at the second longitudinal side edge 54 respectively. The term "connected" includes any means for affixing the flaps 37 to the outer covering layer 11 and encompasses means whereby the flaps 37 are made integral with the outer covering layer 11 (i.e., the flaps 37 are a separate element affixed to the outer covering layer 11) and means whereby the flaps 37 are unitary with the outer covering layer 11 (i.e., the flaps 37 have at least one continuous and undivided element in common with the outer covering layer 11). In the preferred diaper construction shown in FIGS. 2 and 3, the flaps 37 are connected to the covering layer 11 adjacent to the first and second longitudinal side edges 52 and 54 of the absorbent core 14 so that when the diaper is worn the flaps 37 will encircle the legs of the wearer. If other diaper constructions are used other placements of the flaps 37 may be necessary.

The distal edge 42 is elastically contractible having a stretched length (i.e., a length when subjected to a tensile force sufficient to over-come the contractive forces of the elastic element 44) which is at least about 110% of its contracted length (i.e., the length of the distal edge 42 when not tensile forces are applied and the contractive forces of the elastic element 44 are allowed to contract the distal edge 42). Thus, the distal edge 42 is the line spaced farthest from the fixed edge 40 (which distance is measured along the liquid contacting surface 43 of the flaps 37) along which elastic contraction occurs.

The distal edge 42 is preferably displaced from the absorbent core 14 a distance sufficient to permit the flaps 37, which are flexible, to be gathered about the legs of the wearer without major gaps being formed between the flaps 37 and the wearer's legs. As used herein, the term "displaced" includes distal edges 42 which are displaceable from the absorbent core 14. In other words, if the distal edge 42 may assume more than one position relative to the absorbent core 14 with equal facility then that distal edge 42 is displaceable and included in the term "displaced" even though the distal edge 42 may assume a position adjacent to the absorbent core 14 at some times. The distance from the distal edge 42 to the absorbent core 14 is measured along a line drawn from the distal edge 42 to the closest part of the absorbent core 14 when the distal edge 42 is positioned so as to be spaced from the absorbent core 14 as far as possible. Preferably, the distal edge 42 will be displaced from the absorbent core 14 a distance of at least about 0.25 inches (6.3 mm). Most preferably the distal edge 42 will be displaced at least about 0.50 inches (13 mm) and still more preferably at least about 0.75 inches (19 mm).

While the flaps 37 may be manufactured from an elastic material or otherwise made the be elastically contractible the required elasticity is preferably provided by an elastic element 44. The elastic element 44 is affixed to the flaps 37 in an elastically contractible condition so that in a normally unrestrained configuration, the elastic element 44 effectively contracts or gathers the flap material adjacent to the elastic element 44. The placement of the elastic element 44 will determine the location of the distal edge 42 as hereinbefore described. The elastic element 44 may be affixed to the flaps 37 in an elastically contractible condition in at least two ways. For example, the elastic element 44 may be stretched to its stretched condition and fixed to the flaps 37 while the flaps 37 are in an uncontracted condition. Alternatively, the flaps 37 may be contracted, for example, by pleating, and the elastic element 44 fixed to the contracted flaps 37 while the elastic element 44 is in its relaxed or unstretched condition.

The elastic element 44 preferably develops a skin contact pressure in use of from about 0.1 to about 2.5 pounds per square inch (about 0.7 to about 17 kpa). A skin contact pressure within that range is acceptable to provide continued contact of the flaps 37 with the infant's thigh without exerting a pressure which detrimentally indents or marks the skin. To provide the proper skin contact pressure, the elastic element 44 will preferably have a contractional force in its stretched condition in the range of from about 10 to about 200 grams and most preferably in the range of from about 20 to about 100 grams. The elastic element 44 should provide such a contractional force and thus establish its stretched condition at an elongation from its relaxed state in the range of from about 50 to about 400 percent and most preferably in the range of from about 125 to about 300 percent.

One elastic member 44 which has been found to work well is an elastic tape having a cross-section of 0.007 inches by 0.06 inches and made from natural rubber which is available from East Hampton Rubber Company and identified by them as L-1900 Rubber Compound. The elastic tape produces a contractual force of about 50 grams when stretched 150 percent from its relaxed condition. The rubber tape was used as the elastic element 44 in the preferred embodiment of FIGS. 2 and 3 and was stretched 150 percent from its relaxed condition to place it in its stretched condition, i.e., its maximum stretched length as allowed by the materials used for the flaps 37 when attached to the flaps 37, and has a tension therewithin of about 50 grams.

The elastic element 44, as shown in FIGS. 2 and 3, is operatively associated with the flaps 37 by securing it to the flaps 37 with an elastic attachment means (not shown). The elastic attachment means should be flexible and of sufficient adhesiveness to hold the elastic element 44 in its stretched condition substantially indefinitely. One material which has worked as a flexible elastic attachment means is hot melt adhesives such as marketed by Findley Adhesives, Inc., Elm Grove, Wisconsin, under the tradename Findley Adhesives 691-336. A more detailed description of how the elastic element 44 may be positioned and secured to the diaper 10 is given in the hereinbefore referenced U.S. Pat. No. 3,860,003 entitled "Contractible Side Portions For Disposable Diaper" which issued to K. B. Buell on January 14, 1975.

In the preferred embodiment illustrated in FIG. 2 the flaps 37 are unitary with the outer covering layer 11. More specifically, the backsheet portion 16 is sufficiently wide so that the material used for the backsheet portion 16 extends beyond the longitudinal seams 32. In this embodiment, the material used for the backsheet portion 16 flaps 37 with the edge of the backsheet portion material adjacent the longitudinal seams 32 forming the fixed edge 40 of the flaps 37.

The liquid contacting surface 43 of each flap 37 is provided with leakage resistant portion 48 (FIG. 3). The leakage resistant portion 48 is a portion of the flaps 37 positioned between the distal edge 42 and the fixed edge 40 of the flaps 37. The leakage resistant portion 48 retards the movement of liquid from the fixed edge 40 of the flaps 37 to the distal edge 42 of the flaps 37. The leakage resistant portion 48 thereby provides an obstacle in the path followed by liquid as it tends to move across the liquid contacting surface 43 from the point of discharge toward the distal edge 42 from which liquid leakage can occur. Accordingly, the leakage resistant portion 48 is non-wicking (i.e., liquid contacting the leakage resistant portion 48 will not cross the leakage resistant portion 48 due to capillary liquid transport), non-absorbent (i.e., liquid is not retained by the leakage resistant portion 48 and is therefore free to flow back toward the absorbent core 14), and liquid impermeable. Further, the leakage resistant portion 48 is positioned and dimensioned such that liquid will not pass the leakage resistant portion 48 in normal use of the diaper 10.

In the perferred embodiment illustrated in FIGS. 2 and 3 the leakage resistant portion 48 is a strip of polyethylene film of the same type as used for the backsheet portion 16. Thus, the leakage resistant portion 48 will neither absorb, nor wick liquid. In addition, the leakage resistant portion 48 is impermeable to liquid; thus, liquid will not pass through the thickness of the leakage resistant portion 48 under normal usage and pressures.

Preferably, the leakage resistant portion 48 has a length which extends the entire length of the flaps 37 and a width of at least about 0.125 inches (3 mm). Other dimensions may, however, also be used. For example, the leakage resistant portion 48 may have a length different from the length of the flaps 37. In addition, a variety of widths may be used for the leakage resistant portion 48. While the width of the leakage resistant portion 48 is preferably at least about 0.125 inches (3 mm), it is more preferably at least about 0.25 inches (6 mm) and still more preferably at least about 0.50 inches (12 mm). The larger the width of the leakage resistant portion 48 the less likely liquid is to bridge the leakage resistant portion 48 and thus leak out of the diaper 10.

In use, the diaper 10 is placed between the legs of the diaper wearer and fastened about the wearer's waist using any suitable means such as adhesive tapes 56 as is well known. When the diaper 10 of the present invention is applied to a wearer, it exhibits improved liquid containment characteristics. While not wishing to be bound by any one theory it is believed that the improved liquid containment characteristics are achieved in the following manner.

As urine is discharged onto the topsheet portion 12 some of the urine penetrates the topsheet portion 12 and is absorbed by the absorbent core 14 (hereinafter referred to as absorbed urine), some of the urine flows on the surface of the topsheet portion 12 (hereinafter referred to as surface urine), some of the urine is absorbed by and wicks laterally through the topsheet portion 12 and some of urine flows into the capillary channel formed at the interface between the topsheet portion 12 and the skin of the diaper wearer.

The absorbed urine migrates throughout the absorbent core 14 moving from the point of discharge (i.e., the crotch area 13) toward the peripheral edge 50 of the absorbent core 14. Eventually, the urine will reach the first and second longitudinal side edges 52 and 54 respectively. Since the absorbed urine which encounters the leakage resistant portion 48 is not absorbed by and cannot wick into the flaps 37 the absorbed urine is effectively prevented from leaking out of the diaper 10 at the longitudinal side edges 52 and 54 respectively.

The surface urine, likewise, moves from the point of discharge toward the first and second longitudinal side edges 52 and 54 respectively. Surface urine which contacts the leakage resistant portions 48 is not absorbed. In normal use the gravitational forces will tend to cause the surface urine to drain back toward the absorbent core 14. The surface urine which does cross the leakage resistant portion is retarded from leaking out of the diaper by the sealing affect achieved by the elastic member 44 as it draws the flaps 37 about the legs of the diaper wearer.

The distal edge 42 of the flaps 37 is elastically contractible so that when the diaper 10 is worn the distal edge 42 is drawn about the wearer's legs. The fixed edge 40 normally sags away from the wearer's legs thereby forming a gap between the leakage resistant portion 48 and the skin of the wearer. Liquid flowing along the capillary channel formed between the topsheet portion 12 and the skin of the diaper wearer is prevented from bridging the leakage resistant portion 48 by the discontinuity in the capillary channel at the leakage resistant portion 48. In this manner, liquid is prevented from leaking from the diaper 10.

Finally, urine which is absorbed interstitially by the topsheet portion 12 wicks laterally through the topsheet portion 12 toward first and second longitudinal side edges 52 and 54. As in the instance of the surface urine, the urine absorbed by the topsheet portion 12 encounters the leakage resistant portion 48 which is non-wicking. The urine absorbed by the topsheet portion is thereby prevented from reaching the distal edge 42 from which leakage can occur.

It will be understood by those skilled in the art that the present invention has been described with reference to exemplary embodiments and that variations or modifications can be effected in the described embodiments without departing from the spirit and scope of the invention.

Figure 4:
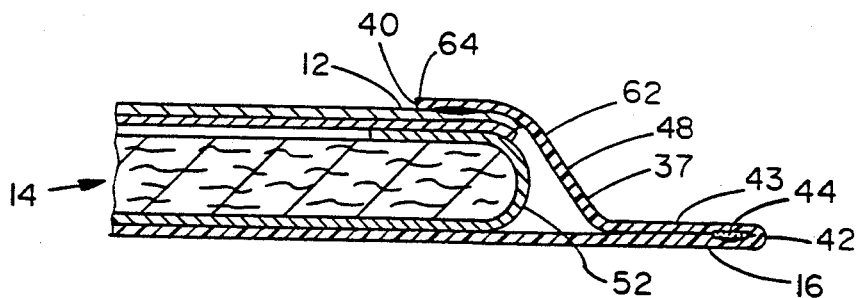
FIG. 4 is a cross-sectional view of an alternatively preferred embodiment of the present invention taken along a line corresponding to line 3—3.
Figure 5:
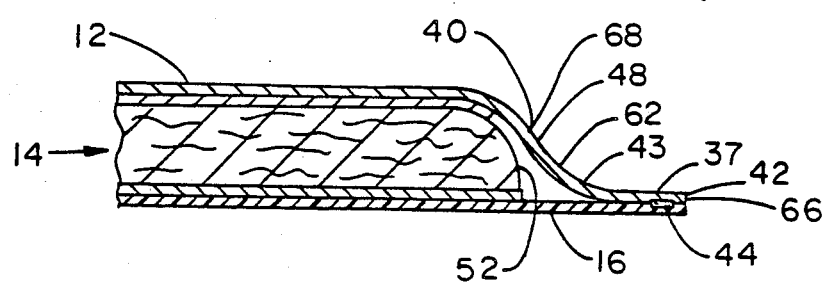
FIG. 5 is a cross-sectional view of an alternatively preferred embodiment of the present invention taken along a line corresponding to line 3—3.
Figure 6:
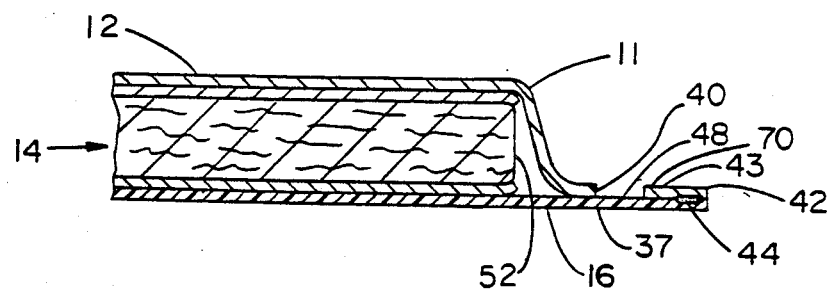
FIG. 6 is a cross-sectional view of an alternatively preferred embodiment of the present invention taken along a line corresponding to line 3—3.

As seen in FIG. 4, for example, the flaps 37 may each be utilized as intermediate members 62, as hereinbefore described, to indirectly join the topsheet portion 12 and the backsheet portion 16. FIGS. 4, 5, and 6 are crosssectional views of alternatively preferred embodiments of the present invention taken along lines corresponding to line 33 of FIG. 2. While only one edge of the diaper is shown in and described with reference to FIGS. 4, 5, and 6 it should be understood that the edges of the diaper 10 are essentially mirror images of each other.

With reference to FIG. 4 it can be seen that the flaps 37 are formed by extending the material used for the backsheet portion 16 beyond the first longitudinal side edge 52 of the absorbent core 14 and affixing the edge 64 of the material used for the backsheet portion 16 to the topsheet portion 12. The edge 64 thus coincides with the fixed edge 40. The elastic element 44 is secured to the distal edge 42 and the liquid contacting surface 43 is positioned between the fixed and distal edges 40 and 42.

The leakage resistant portion 48 of the liquid contacting surface 43 is positioned between the distal edge 42 and the fixed edge 40. Since the entire flap 37 of the alternatively preferred embodiment of FIG. 4 is manufactured from the same material used for the backsheet portion 16, the leakage resistant member 48 extends from the fixed edge 40 to the distal edge 42.

FIG. 5 shows an alternatively preferred embodiment in which the flaps 37 are utilized as an intermediate member 62 to indirectly join the topsheet portion 12 and the backsheet portion 16. The flaps 37 are formed by extending the material used for the topsheed portion 12 beyond the first longitudinal side edge 52 of the absorbent core 14 and affixing the edge 66 of the material used for the topsheet portion 12 to the backsheet portion 16.

The marginal portion 68 of the material used for the topsheet portion 12 is treated so as to be liquid impermeable, non-absorbent, and non-wicking. While such treatments are well known in the art a suitable treatment is obtained by applying a food grade paraffin wax such as is marketed by Boron Oil Co., Cleveland, Ohio, under the tradename Boron Wax.

The treated marginal portion 68 forms the leakage resistant portion 48 of the liquid contacting surface 43. As can be seen in FIG. 5 the fixed edge 40 coincides with the inward edge of the marginal portion 68 while the distal edge 42 is spaced therefrom. The elastic element 44 is affixed to the flaps 37 at the distal edge 42.

FIG. 6 shows an alternatively preferred embodiment in which the flaps 37 are provided with a facing sheet 70. In this embodiment, the material used for this backsheet portion 16 extends beyond the first longitudinal side edge 52 of the absorbent core 14 to form flaps 37 which are unitary with the backsheet portion 16. The topsheet portion 12 is directly joined to the backsheet portion.

The fixed edge 40 of the flaps 37 is connected to the outer covering layer 11 and the elastic element 44 is affixed at the distal edge 42. To prevent direct contact between the elastic element 44 and the skin on the wearer a facing sheet 70 is affixed to the distal edge 42. The facing sheet 70 may be of any flexible material which is non irritating to the skin. In the preferred embodiment illustrated the facing sheet 70 was manufactured from the same material as was used for the topsheet portion 12.

The leakage resistant portion 48 of the liquid contacting surface 43 is positioned between the fixed edge 40 and the distal edge 42.

We claim:

1. A disposable diaper having a front waist portion, a back waist portion, and a crotch portion positioned between said front waist portion and said back waist portion, the disposable diaper comprising:
   an outer covering layer;
   an absorbent core means for absorbing liquid, said absorbent core means being encased in said outer covering layer;
   a multiplicity of flaps, each of said flaps having a fixed edge, a distal edge in spaced relation to said fixed edge, and a liquid contacting surface, the sides of which are bounded by said fixed and said distal edges, each of said flaps having said fixed edge connected to said outer covering layer, said flaps being a separate element affixed to said outer covering layer, said distal edge being displaced from said absorbent core means, each of said flaps having a leakage resistant portion interposed on said liquid contacting surface between said fixed edge and said distal edge, said leakage resistant portion being liquid impermeable; and
   an elastic element, said elastic element being operatively associated with said distal edge of said flaps and secured in an elastically contractible condition to said flap adjacent at least two ends to render said distal edge of said flaps elastically contractible so that said elastic element effectively contracts or gathers the flap material.

2. The disposable diaper of claim 1 wherein said distal edge is curvilinear.

3. The disposable diaper of claim 2 wherein said fixed edge and said distal edge are non-parallel to each other.

4. The disposable diaper of claim 1 wherein said distal edge is rectilinear.

5. The disposable diaper of claim 4 wherein said fixed edge and said distal edge are parallel to each other.

6. The disposable diaper of claim 4 wherein said fixed edge and said distal edge are non-parallel to each other.

7. The diposable diaper of claim 1 wherein said outer covering layer comprises a topsheet portion and a backsheet portion, said topsheet portion being joined together with said backsheet portion.

8. The disposable diaper of claim 7 wherein said flaps are affixed to said backsheet.

9. The disposable diaper of claim 7 wherein said flaps are affixed to said topsheet.

10. The disposable diaper of claim 9 wherein said absorbent core means is of an hourglass shape.

11. The disposable diaper of claim 10 wherein said absorbent core means has longitudinal side edges, said fixed edge being connected to said topsheet adjacent said longitudinal side edge of said absorbent core in at least said crotch portion.

12. The disposable diaper of claim 11 wherein said distal edge is rectilinear.

13. The disposable diaper of claim 12 wherein said distal edge and said fixed edge are parallel to each other.

14. A disposable diaper comprising:
    an outer covering layer comprising a backsheet portion and a topsheet portion;
    an absorbent core means for absorbing liquid, said absorbent core means being encased in said outer covering layer;
    a multiplicity of flaps, each of said flaps having a fixed edge, a distal edge in spaced relation to said fixed edge, and a liquid contacting surface bounded by said fixed and said distal edges, each of said flaps having said fixed edge connected to said outer covering layer, said distal edge being displaced from said absorbent core means, each of said flaps having a leakage resistant portion interposed on said liquid contacting surface between said fixed edge and said distal edge, said leakage resistant portion being liquid impermeable, and said flaps being manufactured from an elastic material to render such flaps elastically contractible so that the flap material is contracted or gathered.

15. The disposable diaper of claim 14 wherein each of said flaps is unitary with said outer covering layer.

16. The disposable diaper of claim 15 wherein each of said flaps is unitary with said topsheet portion.

17. The disposable diaper of claim 14 wherein each of said flaps is a separate element affixed to said outer covering layer.

18. The disposable diaper of claim 17 wherein each of said flaps if affixed to said topsheet portion.

19. A disposable diaper having a front waist portion, a back waist portion, and a crotch portion positioned between said front waist portion and said back waist portion, the disposable diaper comprising:
    an outer covering layer;
    an absorbent core means for absorbing liquid, said absorbent core means being encased in said outer covering layer;
    a multiplicity of flaps, each of said flaps having a fixed edge, a distal edge in spaced relation to said fixed edge, and a liquid contacting surface, the sides of which are bounded by said fixed and said distal edges, each of said flaps having said fixed edge connected to said outer covering layer, said distal edge being displaced from said absorbent core means; and
    an elastic element, said elastic element being operatively associated with said distal edge of said flaps and secured in an elastically contractible condition to said flap adjacent at least two ends to render said distal edge of said flaps elastically contractible so that said elastic element effectively contracts or gathers the flap material.

20. The disposable diaper of claim 19 wherein each of said flaps is unitary with said outer covering layer.

21. The disposable diaper of claim 19 wherein each of said flaps is a separate element affixed to said outer covering layer.

22. The disposable diaper of claim 19 wherein said outer covering layer comprises a topsheet portion and a backsheet portion, said topsheet portion being joined with said backsheet portion.

23. The disposable diaper of claim 22 wherein said flaps are connected to said backsheet.

24. The disposable diaper of claim 23 wherein each of said flaps is unitary with said backsheet.

25. The disposable diaper of claim 23 wherein each of said flaps is a separate element affixed to said backsheet.

26. The disposable diaper of claim 22 wherein said flaps are connected to said topsheet.

27. The disposable diaper of claim 26 wherein each of said flaps is unitary with said topsheet.

28. The disposable diaper of claim 26 wherein each of said flaps is a separate element affixed to said topsheet.

* * * * *

Disclaimer 4,909,803.—*Mohammed I. Aziz*, Cincinnati; *Ted L. Blaney*, West Chester, both of Ohio. DISPOSABLE ABSORBENT ARTICLE HAVING ELASTICIZED FLAPS PROVIDED WITH LEAKAGE RESISTANT PORTIONS. Patent dated Mar. 20, 1990. Disclaimer filed Feb. 5, 1990, by the assignee, The Proctor and Gamble Co.

The term of this patent subsequent to Feb. 28, 2006, has been disclaimed.
[ *Official Gazette May 29, 1990* ]